United States Patent [19]

Spickermann

[11] Patent Number: 6,051,188
[45] Date of Patent: *Apr. 18, 2000

[54] PROCESS AND DEVICE FOR THE DISINFECTION OF A MEDICAL APPARATUS

[75] Inventor: Reiner Spickermann, Wasserlosen-Burghausen, Germany

[73] Assignee: Fresenius Medical Care Deutschland GmbH, Bad Homburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/942,584

[22] Filed: Oct. 2, 1997

[30] Foreign Application Priority Data

Oct. 2, 1996 [DE] Germany ............... 196 40 839

[51] Int. Cl.$^7$ ....................................... A61L 2/18
[52] U.S. Cl. ................. 422/30; 422/31; 422/37; 422/292
[58] Field of Search ................. 422/29, 30, 44, 422/105, 292, 31, 37; 204/157.48

[56] References Cited

U.S. PATENT DOCUMENTS

| | | |
|---|---|---|
| 3,819,329 | 6/1974 | Kaestner et al. . |
| 4,035,981 | 7/1977 | Braun et al. . |
| 4,141,830 | 2/1979 | Last . |
| 4,230,571 | 10/1980 | Dadd . |
| 4,610,782 | 9/1986 | Tersteegen et al. . |
| 4,963,341 | 10/1990 | Huxtable et al. . |
| 5,015,541 | 5/1991 | Evans . |
| 5,139,675 | 8/1992 | Arnold et al. ................ 210/636 |
| 5,275,784 | 1/1994 | Perlaky . |
| 5,292,488 | 3/1994 | Cerola et al. . |
| 5,306,352 | 4/1994 | Nicolson et al. . |
| 5,316,740 | 5/1994 | Baker et al. ................ 422/186.07 |
| 5,407,550 | 4/1995 | Shimamune et al. . |
| 5,484,397 | 1/1996 | Twardowski ................ 604/5 |
| 5,585,003 | 12/1996 | Van Hewenhizen ................ 210/646 |
| 5,593,598 | 1/1997 | McGinness et al. ................ 210/748 |
| 5,603,897 | 2/1997 | Heiler et al. ................ 422/30 |
| 5,641,456 | 6/1997 | Rosenauer ................ 422/29 |
| 5,776,351 | 7/1998 | McGinness et al. ................ 210/748 |

FOREIGN PATENT DOCUMENTS

| | | |
|---|---|---|
| 0 364 367 | 4/1990 | European Pat. Off. . |
| 722740 | 7/1996 | European Pat. Off. . |
| 24 28 256 | 1/1976 | Germany . |
| 41 38 140 | 12/1993 | Germany . |
| 2094992 | 9/1982 | United Kingdom . |
| WO 93/09821 | 5/1993 | WIPO . |

OTHER PUBLICATIONS

Block, Seymour S., ed. Disinfection Sterilization and Preservation, 4th ed., pp. 553–555, 1991.

Translation provided. Holleman–Wiberg, Lehrbuch der Anorganischen Chemie, Textbook of Inorganic Chemistry, Walter de Gruyter, pp. 458–459, 1985.

*Primary Examiner*—Elizabeth McKane
*Attorney, Agent, or Firm*—Kenyon & Kenyon

[57] ABSTRACT

The invention relates to a process for disinfection of a medical apparatus, in particular a dialysis machine, comprising disinfection of areas of the apparatus that are to be kept germ-free, and catalytic decomposition of the disinfectant, in particular NaOCl, used for this purpose, as well as a device for carrying out this process.

31 Claims, 1 Drawing Sheet

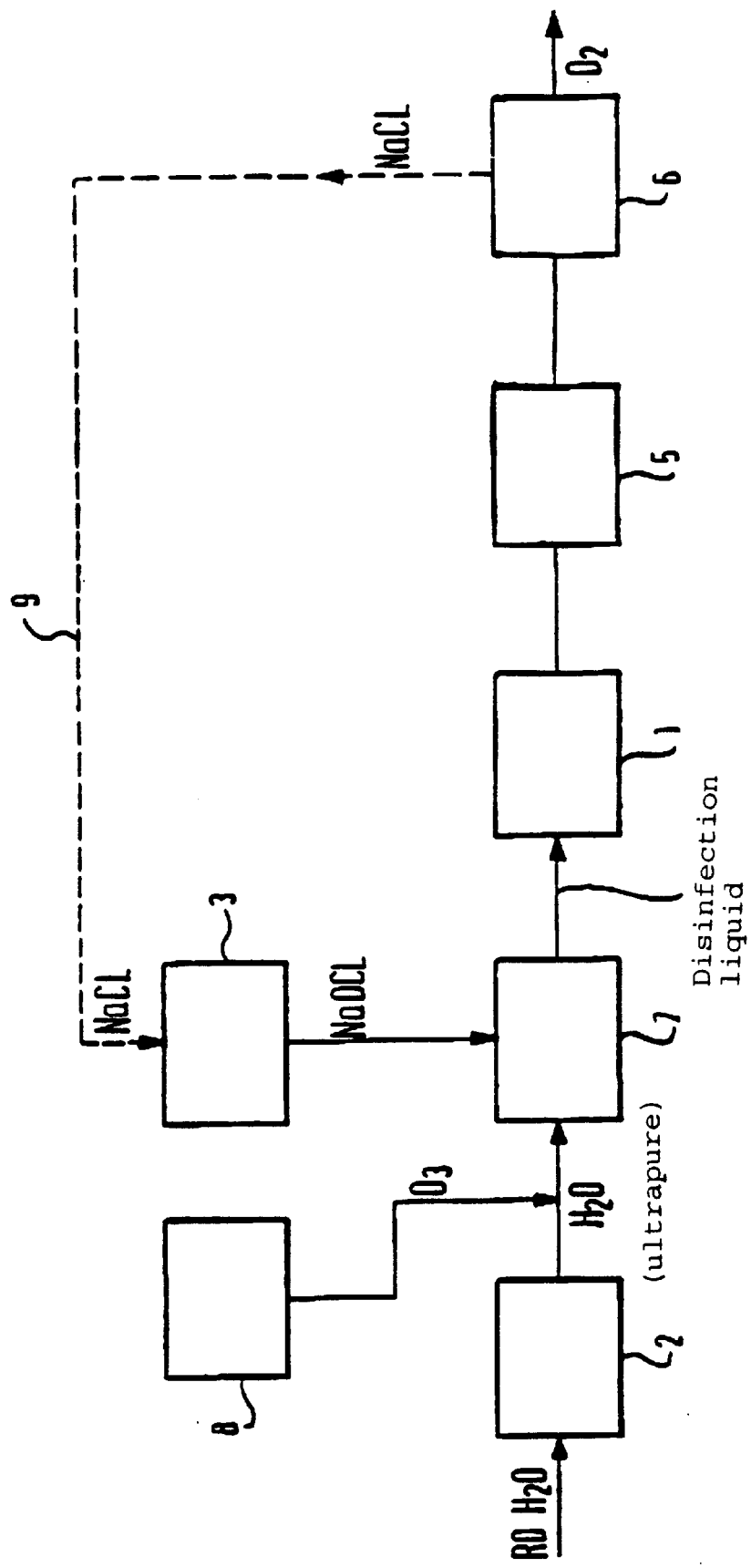

PROCESS AND DEVICE FOR THE DISINFECTION OF A MEDICAL APPARATUS

FIELD OF THE INVENTION

The invention relates to a process and device for the disinfection of a medical apparatus.

BACKGROUND OF THE INVENTION

Medical apparatus, such as dialysis machines, must be disinfected or brought into as sterile a condition as possible at regular intervals.

This shall be illustrated by taking a dialysis machine as an example:

The blood of a patient flows through an extracorporeal blood circulation for purification by a dialysis machine, in which the necessary purification steps are carried out.

Because the dialysate comes into indirect contact with the blood through the dialysis membrane, the dialysis circulation must be kept as sterile as possible. Any toxins that may be present could otherwise get into the patient's blood through the membrane.

The active substance most frequently used for the disinfection of dialysis machines worldwide is NaOCl (bleach). But this highly effective disinfecting and bleaching agent causes considerable environmental pollution. In this connection, mention should be made of the sewage problems. On the other hand, NaOCl has the advantages of being easy to handle and producing effective purification/disinfection. Moreover, in many countries NaOCl is often the only available disinfecting agent and, in addition, it is relatively reasonable in cost.

OBJECTS AND SUMMARY OF THE INVENTION

The object of the invention is, therefore, to make available a process and a device for the disinfection of medical apparatuses which make possible the use of disinfectants without hazard for the environment.

This object is achieved by a process, or by a device adapted to carry out a process, wherein the areas of the apparatus to be kept germ-free are disinfected with disinfectant and the disinfectant used for this purpose is then subjected to catalytic decomposition.

With the process according to the invention and the device according to the invention, it is now possible for the first time to disinfect medical apparatuses such as, for example, dialysis machines with the use of, e.g., NaOCl or $O_3$, without stress or hazard to the environment.

In accordance with one advantageous embodiment of the process according to the invention and/or the device according to the invention, means are moreover provided for the UV photo-oxidation of reverse-osmosis (RO) water to produce ultrapure water. The ultrapure water thus produced can be used, for example, for rinsing the device after disinfection but also when producing ultrapure dialysis liquid from dialysis liquid concentrate.

The NaCl produced by catalytic decomposition can again be reconverted, at least partially, into NaOCl by means of an electrolytic reaction. This NaOCl can again be conveyed back to the disinfection circulation.

According to another advantageous embodiment, the disinfectant content of the disinfecting liquid used is determined. It can thus be established if the disinfectant content in the disinfecting liquid ensures adequate disinfection of the apparatus. Moreover, before a patient is connected to a dialysis device, there must be assurance that all disinfectant has been rinsed out of the apparatus.

The determination of the content of disinfectant occurs preferably immediately during and/or after the catalytic decomposition of the NaOCl.

It is advantageous for the determination of the disinfectant content to be determined by means of a redox electrode. This method has proven to be very simple and reliable and can easily be incorporated in a dialysis machine, thus making possible the further automation of the dialysis procedure.

DESCRIPTION OF THE DRAWING

FIG. 1 is a graphical representation of an embodiment of the invention.

DETAILED DESCRIPTION OF THE PREFERRED EMBODIMENTS

An example of an embodiment of the invention is illustrated in greater detail below on the basis of the drawing, in which FIG. 1 schematically describes the steps of the process according to the invention. It should be pointed out that the steps of the process described can be carried out by suitable means inside the dialysis machine. But it is likewise possible to connect a conventional dialysis machine externally with such means.

Blood from a patient is supplied to a central dialysis unit 1 and purified, i.e., dialyzed, in this dialysis unit 1. The blood is then supplied back to the patient. The present invention effects a disinfection of the lines and/or sections of the dialysis unit through which the dialysate flows. If the blood side consists of one-way parts, disinfection will not be necessary as a rule.

RO water is supplied to a UV photo-oxidation chamber 2. There the water is exposed to UV radiation, for example, the UV radiation of a low-pressure mercury lamp. UV light in the spectral range of 200–300 nanometers kills microorganisms by destroying the DNA of the cells. Low-pressure mercury lamps produce the greatest energy at a wave length of 254 nanometers. This level is very close to the optimal wave length for sterilization, which is 260 nanometers.

Specially developed lamps, in which only high-purity quartz is used, further permits radiation of a wave length at 185 nm. The combined effect that occurs from the UV light at the wavelengths of 185 nm and 254 nm produces the photo-oxidation of dissolved organic compounds.

The emission of UV light at 185 nm further catalyzes the reaction of oxygen dissolved in water to ozone.

Altogether, ultrapure water can be produced by UV photo-oxidation of the RO water. If necessary, additional ozone can be added to this ultrapure water, as is schematically shown in the drawing.

The added ozone can be produced by means of an ozone generator, for example, through a lead dioxide electrode or by means of a Siemens generator 8. The use of the electrolytic oxidation process with lead dioxide anodes offers advantages compared to other generation processes in that there is no formation of gas and that high concentrations can be achieved. There are, of course, also other conceivable processes for the production of ozone. Moreover, the supply of ready-made ozone is also possible.

The electrolytic production of NaOCl occurs in a generator 3. In the preferred production process, 10% sodium chloride solution is electrolyzed in such a way that chlorine set free at the positive pole and the NaOH formed at the negative pole react with each other according to the equation $Cl_2+2NaOH=NaOCl+NaCl+H_2O$.

It is likewise conceivable to run the above-mentioned electrolytic reaction of NaCl in previously produced ultra-pure water, so as to be able to dispense with a special supply of NaOCl to the ultrapure water. The disinfectant thus produced is conveyed to the central dialysis unit 1 via a feeder mechanism 7.

Ozone has advantages in that it is less detrimental to a dialysis membrane in cases where the filter remains in the dialysis machine or the machine has additional filters, such as Diasafe or online filters.

It is likewise conceivable in special applications to ensure the disinfection of a medical apparatus solely with ozone.

Ozone can also be advantageously used for the germ-free conservation of water over several days. In particular, a dialysis machine (home dialysis machine) is used only every two to three days. A sufficient ozone content of the water remaining in the machine prevents the growth of micro-organisms until the next use.

To ensure flawless disinfection, a redox electrode 5 is provided, by means of which the redox potential of the disinfection liquid can be determined. This redox electrode serves to verify the presence of disinfectant during the disinfection process in order to ensure the proper course of the disinfection program. It further serves to verify the absence of disinfectant by way of controlling that the central dialysis unit 1 has been properly rinsed clean.

Such a redox electrode can be built into a dialysis machine, using up little space. Verification that the machine has been rinsed clean which now still has to be carried out manually by means of test strips (potassium iodide starch paper, peroxide test, etc.) can be dispensed with.

The provision of a redox electrode makes the simple control of the disinfection program possible and offers an additional protective function for the dialysis.

Finally, the disinfection liquid is supplied to a receiving system with a catalyst device 6, which effects the catalytic decomposition, e.g., of the NaOCl into the components NaCl and $O_2$. Other disinfectants, for example, such as ozone, could likewise be decomposed.

This catalyst device 6 can also be easily incorporated into the dialysis machine. Furthermore, it can be provided externally or centrally for a plurality of machines of a dialysis station.

The NaCl produced, for example, in a catalytic reaction can then be supplied to the NaOCl generator 3 through a conduction system 9. Thus a closed circuit for the production and catalytic decomposition of NaOCl is created. The starting substances NaCl and $H_2O$ react to form NaOCl, which dissociates into NaCl and $O_2$ after its catalytic decomposition.

These starting products represent no hazards. The risk of corrosive injury to the operator of the machine as well as environmental hazards are excluded.

As mentioned, the NaCl formed can be reconveyed to the NaOCl generator. The other starting products can easily be discharged into the sewage. Use of the acidic partial dialysate or dialyzer concentrate which contains NaCl is also conceivable.

The various devices can be arranged inside a dialysis machine. A built-in catalyst is thus made available in the dialysis machine which has important advantages in terms of sewage pollution as compared to conventional machines.

As mentioned, the process according to the invention can be carried out and incorporated in such a dialysis machine.

It is, however, likewise possible to carry out at least one of the steps of the process, such as UV photo-oxidation, generation of NaOCl, production of ozone, determination of the disinfectant content by means of a redox electrode, or the catalytic decomposition of NaOCl, outside the dialysis machine.

What is claimed is:

1. A process for disinfecting a medical apparatus comprising the steps of feeding to the medical apparatus a solution containing NaOCl, contacting the apparatus with the solution, removing the solution from the apparatus, subjecting the NaOCl to catalytic decomposition to NaCl, and providing at least a portion of the NaCl produced through catalytic decomposition of NaOCl to a generator means for production of NaOCl from NaCl.

2. The process of claim 1 wherein the NaOCl is combined with ultrapure water to form an NaOCl solution.

3. The process of claim 2 wherein the ultrapure water is produced by subjecting reverse osmosis water to UV radiation.

4. The process of claim 3 wherein the UV radiation has a wavelength of 200 to 300 nm.

5. The process of claim 3 wherein the UV radiation is provided by a low pressure mercury lamp or by a low pressure mercury lamp in combination with a high purity quartz lamp.

6. The process of claim 1 wherein the NaOCl is produced by electrolysis of NaCl.

7. The process of claim 1 further comprising determining the disinfectant content of a solution containing the disinfectant using a redox electrode.

8. A process for the disinfection of a medical apparatus comprising the steps of contacting the apparatus with a solution containing NaOCl and ozone, subjecting the NaOCl and ozone to catalytic decomposition to NaCl and $O_2$, and providing at least a portion of the NaCl to a generator means for production of NaOCl from NaCl.

9. The process of claim 8 wherein ozone is provided to the apparatus by means of an ozone generator which utilizes a lead dioxide electrode.

10. A process for disinfecting a medical apparatus comprising the steps of combining NaOCl and ozone with ultrapure water to form a disinfecting solution, contacting the apparatus with the disinfecting solution, measuring the disinfectant content in the disinfecting solution, decomposing the NaOCl into NaCl and $O_2$, providing at least a portion of the NaCl to an NaOCl generator wherein NaCl is converted to NaOCl, and providing the NaOCl produced by the NaOCl generator to the disinfecting solution.

11. The process of claim 10 wherein the ultrapure water is produced by subjecting reverse osmosis water to UV radiation.

12. The process of claim 11 wherein the UV radiation is provided by a low pressure mercury lamp and a high purity quartz lamp.

13. The process of claim 10 wherein a redox electrode is used to measure the disinfectant content of a dialysis solution.

14. The process of claim 10 wherein steps of combining NaOCl and ozone with ultrapure water to form a disinfecting solution, contacting the apparatus with the disinfecting solution, measuring the disinfectant content in the disinfecting solution, decomposing the NaOCl into NaCl and $O_2$, providing at least a portion of the NaCl to an NaOCl generator wherein NaCl is converted to NaOCl, and providing the NaOCl produced by the NaOCl generator to the disinfecting solution is carried out within the medical apparatus.

15. The process of claim 10 wherein steps of combining NaOCl and ozone with ultrapure water to form a disinfecting solution, contacting the apparatus with the disinfecting solution, measuring the disinfectant content in the disinfecting solution, decomposing the NaOCl into NaCl and $O_2$, providing at least a portion of the NaCl to an NaOCl generator wherein NaCl is converted to NaOCl, and providing the NaOCl produced by the NaOCl generator to the disinfecting solution is carried out external to the medical apparatus.

16. A system for disinfecting a medical apparatus comprising a disinfecting solution containing NaOCl, a feeding device constructed and arranged to feed the NaOCl solution to the medical apparatus, a removal device constructed and arranged to remove the NaOCl solution from the apparatus, a catalytic decomposition unit for decomposing the NaOCl solution into NaCl and $O_2$, a NaOCl generator, and a return device for providing at least a portion of the NaCl produced by decomposition to a NaOCl generator.

17. The system of claim 16 wherein the NaOCl solution also contains ozone.

18. The system of claim 17 further comprising an ozone generator that utilizes a lead dioxide electrode.

19. The system of claim 16 further comprising a UV radiation source adapted to convert reverse osmosis water to ultrapure water.

20. The system of claim 19 wherein the UV radiation source comprises a low pressure mercury lamp.

21. The system of claim 20 wherein the UV radiation source further comprises a high purity quartz lamp.

22. The system of claim 16 further comprising a redox electrode for measuring the disinfectant content of the disinfecting solution.

23. The system of claim 16 wherein the feeding device is integrated into the medical apparatus to be disinfected.

24. The system of claim 16 wherein the device is external to the medical apparatus to be disinfected.

25. A system for disinfecting a medical apparatus and decomposing the disinfectant, comprising a dialysis unit, a NaOCl source adapted to provide NaOCl to the dialysis unit, a catalytic decomposition unit for decomposing NaOCl to NaCl, a means for providing the NaCl generated by catalytic decomposition to the NaOCl source, a generator for converting the NaCl to NaOCl, and means for measuring the disinfectant content of the disinfecting solution.

26. The system of claim 25 further comprising an ozone source adapted to provide ozone to the dialysis unit.

27. The system of claim 25 further comprising a UV radiation source adapted to convert reverse osmosis water to ultrapure water, and means for combining NaOCl and the ultrapure water to form a disinfecting solution.

28. A process for disinfecting a dialysis machine comprising the steps of feeding to the dialysis machine a solution containing a disinfectant capable of being catalytically decomposed, contacting the flow path of the dialysis machine, subjecting the disinfectant to catalytic decomposition online in the dialysis machine and removing the solution from the dialysis machine.

29. The process of claim 28 wherein the disinfectant is NaOCl.

30. The process of claim 28 further comprising determining the disinfectant content of a solution containing the disinfectant using a redox electrode.

31. A process for disinfecting a medical apparatus comprising the steps of feeding to the medical apparatus a solution containing a disinfectant capable of being catalytically decomposed, contacting the apparatus with the solution, removing the solution from the apparatus, subjecting the disinfectant to catalytic decomposition and providing a portion of the decomposed disinfectant to a generator means for generation of the disinfectant.

\* \* \* \* \*